US007939266B2

(12) United States Patent
Stuhler et al.

(10) Patent No.: US 7,939,266 B2
(45) Date of Patent: May 10, 2011

(54) TREATMENT OF TRANSFORMED OR INFECTED BIOLOGICAL CELLS

(75) Inventors: Gernot Stuhler, Tuebingen (DE); Helmut Salih, Tuebingen (DE)

(73) Assignee: Eberhard-Karls-Universität Tübingen Universitätsklinikum, Tuebingen (DE)

(*) Notice: Subject to any disclaimer, the term of this patent is extended or adjusted under 35 U.S.C. 154(b) by 1036 days.

(21) Appl. No.: 10/961,320

(22) Filed: Oct. 8, 2004

(65) Prior Publication Data

US 2006/0046971 A1   Mar. 2, 2006

(30) Foreign Application Priority Data

Aug. 26, 2004  (EP) ..................................... 04020259

(51) Int. Cl.
*G01N 33/53* (2006.01)
(52) U.S. Cl. ......................................................... 435/7.1
(58) Field of Classification Search ........................ None
See application file for complete search history.

(56) References Cited

U.S. PATENT DOCUMENTS

| 6,495,664 | B1 | 12/2002 | Cubitt | ............................ | 530/350 |
| 2005/0112700 | A1* | 5/2005 | Perez et al. | ..................... | 435/7.2 |

FOREIGN PATENT DOCUMENTS

| EP | 1 207 395 A1 | 5/2002 |
| EP | 1 233 060 A2 | 8/2002 |
| WO | WO 01/07638 A2 | 2/2001 |
| WO | WO 2004/022773 A1 | 3/2004 |
| WO | WO 2004/042404 | * 5/2004 |
| WO | WO 2004/068139 A2 | 8/2004 |

OTHER PUBLICATIONS

Irish et al. Cell 118:217-228, 2004.*
Buggins et al. J. Immunol. 167:6021-6030; 2001.*
Cell Signaling Technology Catalog; Phospho-Rb Antibody #2181; p. 1.*
"Use of an Oriented Peptide Library to Determine the Optimal Substrates of Protein as Kinases", Songyang et al., Current Biology, vol. 4, No. 11, 1994, pp. 973-982.
"Selective Inhibition of the Platelet-Derived Growth Factor Signal Transduction Pathway by a Protein-Tyrosine Kinase Inhibitor of the 2-phenylaminopyrimidine Class", Buchdunger et al., Proc. Natl. Acad. Sci., vol. 92, Mar. 1995, pp. 2558-2562.
"Effects of a Selective Inhibitor of the Abl Tyrosine Kinase on the Growth of Bcr-Abl Positive Cells", Druker et al., Nature Medicine, vol. 2, No. 5, May 1996, pp. 561-566.
"A Structural Basis for Substrate Specificities of Protein Ser/Thr Kinases: Primary Sequence Preference of Casein Kinases I and II, NIMA, Phosphorylase Kinase, Calmodulin-Dependent Kinase II, CDK5, and Erk1", Songyang et al., Molecular and Cellular Biology, vol. 16, No. 11, Nov. 1996, pp. 6486-6493.
"The Structural Basis for Specificity of Substrate and Recruitment Peptides for Cyclin-Dependent Kinases", Brown et al., Nature Cell Biology, vol. 1, Nov. 1999 pp. 438-443.
"The Hallmarks of Cancer", Hanahan et al., Cell, vol. 100, Jan. 7, 2000, pp. 57-70.

"Structural Mechanism for STI-571 Inhibition of Abelson Tyrosine Kinase", Schindler et al., Science, vol. 289, Sep. 15, 2000, pp. 1938-1942.
"Modelling the Molecular Circuitry of Cancer", Hahn et al., Nature Reviews, vol. 2, May 2002, pp. 331-341.
"Rules for Making Human Tumor Cells", Hahn et al., New England Journal of Medicine, vol. 347, No. 20, Nov. 14, 2002, pp. 1593-1603.
"Recycling the Cell Cycle: Cyclins Revisited", Murray, Cell, vol. 116, Jan. 23, 2004, pp. 221-234.
"Development of a Human Adaptive Immune System in Cord Blood Cell-Transplanted Mice", Traggiai et al, Science, vol. 304, Apr. 2, 2004, pp. 104-107.
"Cancer Immunotherapy: A Treatment for the Masses", Blattman et al., Science, vol. 305, Jul. 9, 2004, pp. 200-205.
"Single Cell Profiling of Potentiated Phospho-Protein Networks in Cancer Cells", Irish et al., Cell, vol. 118, Jul. 23, 2004, pp. 217-228.
"Caged Phosphopeptides Reveal a Temporal Role for 14-3-3 in G1 Arrest and S-phase Checkpoint Function", Nguyen et al., Nature Biotechnology, vol. 22, No. 8, Aug. 2004, pp. 993-1000.
"Cytostatic Anticancer Drug Development", Gardner et al., Journal of Experimental Therapeutics and Oncology, vol. 4, 2004, pp. 9-18.
"A Genetically Encoded Fluorescent Reporter of Histone Phosphorylation in Living Cells", Lin et al., Angew. Chem. Int. Ed. 43, 2004, pp. 2940-2943.
"The Structural Basis for Specificity of Substrate and Recruitment Peptides for Cyclin-Dependent Kinases", Brown et al., Nature Cell Biology, vol. 1, No. 7, Nov. 1999, pp. 438-443.
"Site-Specific Phosphorylation of Retinoblastoma Protein Due to Different Cyclin-Dependent Kinase Activities in Childhood Acute Lymphoblastic Leukemia (ALL)", Hirt et al., W.B. Saunders Company, vol. 98, No. 11, Part 2, Nov. 16, 2001, 1 page.
International Search Report in PCT/EP2005/008976 dated Jan. 12, 2006.
Website http://www.physiomics-plc.com/Q3.htm.
"Constitutive Expression of Functional 4-1BB (CD137) Ligand on Carcinoma Cells," Salih et al., American Association of Immunologists, Copyright 2000, pp. 2903-2910.
"Transcriptional Regulation and Function During the Human Cell Cycle," Cho et al., Nature Genetics, vol. 27, Jan. 2001, pp. 48-54.
"Cancer Genes and the Pathways They Control," Vogelstein et al., Nature Medicine, vol. 10, No. 8, Aug. 2004, pp. 789-799.
"Multiple Ras Effector Pathways Contribute to $G_1$, Cell Cycle Progression," Gille et al., The Journal of Biological Chemistry, vol. 274, No. 31, Jul. 30, 1999, pp. 22033-22040.
"Growth-Factor-Dependent Mitogenesis Requires Two Distinct Phases of Signalling," Jones et al., Nature Cell Biology, vol. 3, Feb. 2001. pp. 165-172 (with supplementary information, pp. 1-3).
"Regulation of Ras Signaling by the Cell Cycle," Stacey et al., Current Opinion in Genetics & Development, vol. 12, pp. 44-46, 2002.
Website http://www.infobiogen.fr/services/chromcancer, Jul. 2006.
Website http://www.ncbi.nlm.nih.gov/entrez/query.fcgi?CMD=searc&DB=omim, Aug. 2006.
Website http://www.nature.com/horizon/chemicalspace/highlights/s5-spec1.html, Aug. 2006.
Website http://invitrogen.com, Jul. 2006.

* cited by examiner

*Primary Examiner* — Michael Burkhart
(74) *Attorney, Agent, or Firm* — Marshall, Gerstein & Borun LLP

(57) ABSTRACT

The present invention relates to a therapeutic or/and diagnostic substance. Furthermore it relates to an expression vector, to a composition comprising the afore-mentioned substance or/and the afore-mentioned expression vector, a method for diagnosing a tumor disease or/and an infectious disease in a living being, as well as to a method for the treatment of a tumor disease or/and of an infection in a living being.

5 Claims, 1 Drawing Sheet

TREATMENT OF TRANSFORMED OR INFECTED BIOLOGICAL CELLS

CROSS REFERENCES TO RELATED APPLICATIONS

This application claims priority of the non-published European patent application EP 040 20 259 filed on Aug. 26, 2004 with the European Patent Office, which is incorporated herein by reference.

BACKGROUND OF THE INVENTION

1. Field of the Invention

The present invention relates to a therapeutic or/and diagnostic substance. Furthermore it relates to an expression vector, to a composition comprising the afore-mentioned substance or/and the aforementioned expression vector, a method for diagnosing a tumor disease or/and an infectious disease in a living being, as well as to a method for the treatment of a tumor disease or/and of an infection in a living being.

2. Related Prior Art

Therapeutic and diagnostic substances which are used in the therapy and diagnosis of tumor diseases or infections, are generally known in the art.

A therapeutic approach in the treatment of tumor and infectious diseases relates to the administration of drugs which cause a damage, necrosis, or growth inhibition of the tumor cells or infected cells.

The so-called cytostatics constitute a group of mostly synthetically produced and chemical heterogeneous substances which have toxic defects on different biological cells, and inhibit cell growth and cell division.

The cytostatic or cytotoxic substances, respectively, which are available so far, do not have a selective effect on tumor cells but harm normal tissue as well. Especially affected are tissues with high cell division rates, as, for example, gonads, hair follicles, and cells of the blood-forming system. An overview about the development of cytostatic is given in S. N. Gardner and H. Fernandes (2004), "Cytostatic Anticancer Drug Development", J. Exp. Ther. Oncol., pages 9 to 18.

Improvements in the treatment and diagnosis of tumor and infectious diseases were made after the discovery of antigens which are expressed on the surface of infected or transformed cells. Such surface proteins on tumor cells are referred to as so-called tumor antigens. Based on these findings, there are efforts to develop substances which specifically recognize these tumor antigens and thereupon mediate a selective attack on the tumor cell. This is for example attempted by means of antibodies specific for these tumor antigens, which are coupled to cytotoxic substances. Another corresponding approach relates to a specific stimulation of the immune system against tumor cells by administering these tumor antigens which can be modified, or by the direct application of so-called tumor vaccines containing these tumor antigens. An overview about this therapeutic approach is given in Joseph N. Blattmann and Philip D. Greenberg (2004), "Cancer Immunotherapy: A Treatment for the Masses", Science, Vol. 305, pages 200 to 205.

However, a disadvantage of this approach is that by most of the currently known tumor antigens malignant cells cannot be distinguished from benign neoplasms or even from normal cells, so that a targeted attack on malignant cells is not possible with such antigens or will not give satisfactory results. Furthermore, there are infected and transformed cells described in the art, which show no special immunogenicity at all. In this case, a distinction between these cells and normal cells and, therefore, a targeted therapeutic intervention by the means of surface markers is not possible.

It is also known in the art that in tumor cells regulatory mechanisms are altered when compared with normal cells. The reason for this could be a genetic alteration of signal transduction factors. A summary of genetic alterations in tumor cells can be found in Douglas Hanahan and Robert A. Weinberg (2000), "The Hallmarks of Cancer", Cell, Vol. 100, pages 57 to 70.

Among experts it is known that in certain tumor cells permanent or increased growth signals of structurally intact but amplified surface receptor kinases are transduced into the cell, whereas in normal cells growth impulses are only induced at specific times. Equally, a huge number of tumors have been described to show activating mutations of intracellular factors of the signal transduction cascade, such as for example mutations in the ras protein, a monomeric GTPase having proliferation regulating activity. The ras protein is mutated in 30% of human tumors. This mutation that is mainly described for exocrine pancreas carcinoma and in colon carcinoma, causes the loss of the hydrolytic activity of the ras protein resulting in a permanent active and proliferation-stimulating form of this protein. Also observed in tumor cells is the inhibition or knockout of growth inhibitory factors like the retinoblastoma (Rb) or the p53 protein, the so-called tumor suppressors. A110 described in the art is an alteration of the telonerase activity in tumor cells which is connected with the acquisition of immortalizing properties. These cells have the property that they, unlike normal cells, can be permanently cultivated in cell culture. Further summarizing reports thereto can be found in William C. Hahn and Robert A. Weinberg (2002), "Rules for Making Human Tumor Cells", N. Engl. J. Med., Vol. 347, No. 20, pages 1593 to 1603; or in William C. Hahn and Robert A. Weinberg (2002), "Modelling the Molecular Circuitry of Cancer", Nat. Rev. Cancer, Vol. 2(5), pages 331 to 341.

Irish et al. (2004), "Single Cell profiling of Potentiated Phospho-Protein Networks in Cancer Cells", Cell, Vol. 118, pages 217 to 228, have discovered that several transduction mechanisms which are controlled by the phosphorylation of signal molecules are altered in tumor cells. On account of these findings, the authors drew up tumor-specific multidimensional molecular phospho profiles. However they do not describe in detail how exactly the signal transduction factors in tumor cells are altered in comparison to those in non-tumor cells. Further there is no description about the relation between the altered signal molecules and the cell cycle, since the experiments described in this document were only performed over a very short time period.

Despite of these discoveries regarding altered signal transduction mechanisms in tumor cells, the experts have so far failed in providing a substance that therapeutically or/and diagnostically benefits from these alterations.

SUMMARY OF THE INVENTION

Therefore, it is an object of the present invention to provide a substance which recognizes and combats transformed or/and infected biological cells in a specifically targeted manner, and which does not show the disadvantages of known substances.

This object is achieved by providing a therapeutic or/and diagnostic substance that indirectly or directly reacts with at least two molecules which largely simultaneously appear exclusively in a transformed or/and infected biological cell, said reaction resulting in the induction of a biological or/and detectable property.

According to the invention, a substance is understood to be both, a purely chemically defined substance, like an organic or inorganic compound, as well as a biological substance, like a peptide or a protein or an RNA/DNA aptamere. Therefore, a substance can be a low molecular agent, a so-called "small molecule" as well as a viral or molecularly modified particle or an antibody.

A therapeutic or diagnostic substance refers to a kind of substance that is designated for use in therapeutic or diagnostic applications.

According to the invention, a transformed cell refers to a kind of cell that has undergone a malignant, neo-plastic or oncogenic transformation, i.e. a cell that has undergone an alteration resulting in an altered growth behavior. Causes for such alterations can be chemical or physical noxa as well as an infection by oncogenic viruses. Also spontaneous mutations are observed which lead to a transformation of the affected cell. Frequently, transformed cells acquire the ability to form tumors.

According to the invention, an infected cell refers to a kind of cell which has been penetrated by pathogens, like for example by viruses, bacteria, fungi or microorganisms of all kinds, or parts thereof, which have caused an alteration in the cell. In connection with this invention, this particularly refers to an infection of cells by oncogenic viruses, for example by so-called DNA tumor viruses, such as certain adeno-viruses, papilloma viruses, or herpes viruses, such as the Epstein-Barr virus (EBV). It has for example been shown for EBV that after an infection, homologs of kinases are expressed in the cell, which interfere with the regulation of the signal transduction. Infective pathogens also include representatives of the so-called RNA tumor viruses or retroviruses as well as of organisms in general, which interfere with and alter the signal transduction mechanisms of the infected cell.

According to the invention, this also includes cells which are in direct or indirect contact with a transformed or infected cell, respectively, but which do not necessarily need to be transformed or infected themselves. However, such a cell is directly influenced by or/and itself influencing the altered cell and therefore can decisively contribute to the progression of a tumor or an infectious disease. For this reason, this cell is also especially interesting as a therapeutic target.

The at least two molecules with which the substance according to the invention reacts, refer to cell-owned compounds such as for example enzymes, which differ from each other in their activity or/and specificity or/and affinity for or/and accessibility to reactants or in other characteristics. According to findings of the inventors, these molecules do not appear simultaneously in normal, i.e. in non-transformed or non-infected cells. These differences in the chronological order of appearance of the two molecules, which can be observed in single normal cells, can, for example, be the result of cell cycle-specific regulatory mechanisms. It is, in fact, known that for example cyclin-dependent kinases (CDK) are regulated both in their activity as well as in their availability over the cell cycle, so that these proteins only appear at specific times in the cell cycle. The phenomenon of the non-simultaneous appearance of the molecules in question in single normal cells can be traced back to other regulatory intra- and extra-cellular phenomena, such as for example time-coordinated mitogenic impulses.

According to the invention, non-simultaneous appearance of the two molecules means that these two molecules either are not present at the same time in one normal single cell, or are not active at the same time, or do not display their activity at the same time or in the same manner. That is to say, that simultaneously on the contrary, means that in a transformed or infected cell these two molecules are present or active in one single cell essentially at the same time, i.e. over longer times within the cell cycle or in the arrested state of the cell (G0 phase) and not just punctiform.

This concurrence in transformed or/and infected cells means, according to the invention, that the two molecules appear essentially simultaneously in each single cell.

The reaction of the substance with the at least two molecules can take place in a direct way, i.e. via direct steric interaction of the substance with the two molecules, as well as indirectly, for example via interposed factors or interposed molecules.

The reaction of the substance according to the invention with the two molecules can result, for example, in an addition or separation of molecules or parts of molecules, such as phosphate groups, to and from the substance, or to and from interposed factors, or in a rearrangement of groups or parts of the substance or of interposed factors.

A biological property refers to a property which is specifically induced by the substance due to the reaction with the at least two molecules, and, which for example, presents itself as a biological activity in the cell. In general, said property might refer to an enzymatic, chemical, biochemical or physical activity which is induced by the substance.

According to the invention, a detectable property refers to a property which is induced by the reaction of the substance with the at least two molecules, and presents itself as a measurable value that indirectly or directly emanates from the so-reacted substance. As a detectable property, every measurable property can be considered, e.g. an activity that can be detected by means of chemical, biochemical or physical methods known in the art.

The biological or/and detectable property can be induced as a result of the metabolization of substance in the cell, as a result of the transformation of the substance into a different state of activity or a different structure, or because of the expression of a product produced by the cell, such as an enzyme, or because of the modification of the activity of a cell-owned protein, whereby all this results from the reaction of the substance with the at least two molecules.

Said metabolic or expressed product resulting from the induction of the biological or/and detectable property, or even the reacted substance itself can directly act as a therapeutic or diagnostic agent, can cause an indirect reaction, as for example an immunoreaction, or can act as a mediator by enabling a targeted attack of a therapeutic or diagnostic agent.

According to the invention, due to an appropriate construction of the substance which is up to the discretion of the skilled person, the biological or detectable property that is explained above in more detail, is only induced if said substance reacts with the at least two molecules in an essentially simultaneous manner. A reaction of the substance according to the invention, with only one of the two molecules does not result in the induction of the biological or/and detectable property.

The object underlying the invention is herewith totally achieved.

The inventors have demonstrated for the first time on a single cell level, that intracellular molecules, such as for example factors of the signal transduction cascade, appear essentially simultaneously in a transformed or an infected biological cell. Said molecules are, for example, simultaneously active in the cell cycle over a longer time, whereas such molecules in a normal, i.e. healthy cell appear in a clearly distinguishable chronological order, e.g. are active in the cell cycle at different times.

This phenomenon of the concurrence of the appearance of molecules exclusively in transformed or infected cells, that has been discovered by the inventors is not described in the art. It is known that in larger populations of tumor cells, as for example in cell cultures, tissue structures or whole organs, certain signal molecules are constitutively active. For example, in 30% of all tumors the ras kinase is permanently sending signals into the cell. Therefore, when examining a plurality of transformed cells, a parallel appearance of the ras kinase and other signal molecules, such as CDKs, can be assumed, even if this takes place just in a punctiform manner within the cell cycle. This assumption in the art regarding cell populations does not allow any conclusions to the conditions in a single cell. This has so far prevented the concept of a targeted substance that is effective in each single transformed or/and infected cell.

On the basis of these new findings obtained by the inventors it is now possible for the first time to design the substance according to the invention, which induces a biological or/and diagnostic property in single transformed and infected cells, due to an essentially simultaneous reaction of said substance with the two molecules.

This property is not induced in normal, e.g. healthy cells, since no corresponding reaction is taking place, because of the clearly distinguished chronological order of appearance of the at least two molecules in said cells. Instead of this, in normal cells only a reaction of the substance according to the invention, with only one of the two molecules takes place, since the respective other molecule is not active, present or accessible at the same time, for example due to cell cycle-specific regulations.

The substance can be designed in such a manner, that a reaction of the substance with only one molecule, or a reaction first with one of the two molecules and after a sufficient time period with the respective other molecule, or that no reaction at all results in an instability, a direct or indirect degradation, an inactivation, the discharging or any other inoperativeness of the substance according to the invention. An induction of the biological or/and detectable property in normal or healthy cells does, therefore, not take place.

The inventors have therefore provided a substance that induces effects in transformed and infected cells in a highly selective and specific manner, whereas these effects are essentially not induced in normal cells. Thus, the substance represents a valuable tool in the therapy and in the diagnostics of tumor and infectious diseases.

The substance according to the invention is preferably constructed in such a manner that it reacts with two cellular enzymes, especially with two kinases, which are involved in the regulation of the cell cycle.

The afore-mentioned measure has the advantage, that key factors of the regulation of the cell cycle are utilized in order to induce the biological or/and detectable property. The inventors have found, that for example two enzymes, preferably two kinases or phosphotransferases, are essentially simultaneously active in a transformed or infected cell with no simultaneous action being observed in a healthy cell.

The substance according to the invention is designed in such a way, that it induces the biological or/and detectable property in the cell after the reaction with the two enzymes or two kinases. Such a design which is up to the discretion of a man of the art, is especially useful, since it provides a therapeutic or diagnostic tool that is highly selective for a transformed or infected cell. With this measure, a biological property can also be induced in a cell that has been infected by viruses which are described in the art and which cause an activation of cell cycle-regulating kinases. According to the invention, this also includes kinases which are present in cell cycle-arrested cells, i.e. in such cells which are resting in G0 phase.

According to a preferred further embodiment, the substance according to the invention is designed in such a manner, that the biological or/and detectable property is induced in a case where one of the two molecules is an enzyme of the ras/raf signal transduction cascade, and the other of the two molecules is an enzyme of the CDK2 signal transduction cascade.

The ras/raf signal transduction pathway results in an activation of the MAP kinase (mitogen-activated protein kinase, also called ERK1) via a cascade of, essentially, phorphorylation events; cf. William C. Hahn and Robert A. Weinberg (2002, l.c.). The CDK2 signal transduction pathway results in an activation of the cyclin-dependent kinase 2 via the stimulation of the transcription. According to the invention, the CDK2 kinase can consist of the catalytic subunit cdk2 and the regulatory subunit cyclin A, as well as of the cdk2 subunit and cyclin E subunit. Furthermore, any active CDK2 kinase is considered; cf. for this A. W. Murray (2004), "Recycling the Cell Cycle: Cyclins Revisited", Cell, Vol. 116 (2), pages 221 to 234.

This preferred afore-mentioned measure is advantageous, since it therapeutically and diagnostically utilizes a phenomenon which has been detected by the inventors for the first time as exclusively appearing in transformed and infected cells. It is in fact assumed in the art, that the ras kinase is constitutively active in cultures of tumor cells or other tumor cell populations examined in total, but the kinetics of the kinase activity on a single cell level is, up to now, totally unclear. However, it has now been shown for the first time on a single cell level, that in transformed and infected cells, both the ras/raf as well as the CDK2 signal transduction cascade is largely proceeding simultaneously over longer times, resulting in the simultaneous appearance of the activities of the single factors of the corresponding two signal cascades, such as of, for example, the MAP kinase and the CDK2 kinase, in transformed or infected cells.

This discovery was especially surprising, since in normal, i.e. healthy cells, both signal transduction cascades proceed in a sequential manner. In normal cells the CDK2 kinase complexed with cyclin E usually is active in the late G1 phase or at the beginning of the S phase in which the DNA replication takes place, and CDK2 kinase complexed with cyclin A usually is active a little later in the S phase. On the other hand, in normal cells the MAP kinase is usually active very early in the G1 phase, but no longer at the beginning or during the S phase. As a result of this, as the inventors have shown for the first time, in a normal human dividing cell there is a time difference between the activity peak of CDK2 and the activity peak of MAP kinase, which is about 24 hours.

The simultaneous progression of signal transduction pathways, that is observed in the single transformed and infected cell for a longer time over the cell cycle, with these signal transduction cascades being mutually exclusive in normal cells, has been discovered by the inventors for the first time. The feat of the inventors is that they have made therapeutic use of their observation. In this connection, the inventors have realized that the selectivity of the substance for transformed and infected cells is especially pronounced, if said substance is designed in such a way, that it can react, on the one hand with any enzyme of the ras/raf signal transduction cascade, and on the other hand with any enzyme of the CDK2 signal transduction cascade, so that therewith a biological or/and detectable property is induced.

The substance can also be designed in such a way, that the property in question is induced, when a reaction with enzymes occurs, which are involved in at least two other such signal transduction cascades which do not proceed simultaneously in normal healthy cells. Examples of such enzymes can be found in the online Atlas of Genetics and Cytogenetics in Oncology and Haematology (available on the website of Infobiogen) and the National Center for Biotechnology Information Online Mendelian Inheritance in Man database (available on the website of the National Center for Biotechnology Information), the content of which is incorporated in the present application by reference. Further examples are given in the article of Hahn and Weinberg (2002, l.c.).

According to a preferred embodiment, the substance according to the invention is a substrate for the at least two molecules.

This measure has the advantage that therewith a substance is provided that reacts directly with the two molecules in the envisaged manner, without the need of considering interposed factors. The substance can preferably comprise two different phosphorylation sites, one of the two being, e.g., specifically recognized and phosphorylated by the MAP kinase, and the other one being, e.g., specifically recognized and phosphorylated by the CDK2-kinase. Only the largely simultaneous reaction of the substrate, i.e. the phosphorylation of both the CDK2 phosphorylation site and the MAP kinase phosphorylation site at largely the same time results in the induction of the biological or/and detectable property.

The substance also can be designed in a different way so that it represents a substrate that is, in the case of a largely simultaneous reaction with the two molecules, directly converted into its active form, e.g. due to the establishment of accessibility to active centers or reactive groups of the substance, which have been sterically inaccessible or chemically inactive before the reaction with the two molecules.

Such a design of the substance according to the invention, as a substrate for the two molecules can be managed by a skilled person without undue efforts. For example, the CDK2 and MAP kinase phosphorylation sites which differ from each other, are well known in the art: the CDK2 phosphorylation site is, for example, described in the publication of Brown et al. (1999), "The Structural Basis for Specificity of Substrate and Recruitment Peptides for Cyclin-dependent kinases", Nat. Cell. Biol., Vol. 1(7), pages 438 to 443, and of Songyang et al. (1994), "Use of an Oriented Peptide Library to Determine the Optimal Substrates of Protein Kinases"; Curr. Biol., Vol. 4(11), pages 973 to 982. The phosphorylation site for the MAP kinase is, for example, described in the publication of Songyang et al. (1996), "A Structural Basis for Substrate Specificities of protein Ser/Thr Kinases: Primary Sequence Preference of Casein Kinases I and II, NIMA,. Phosphorylase Kinase, Calmodulin-dependent Kinase II, CDK5, and Erk1", Mol. Cell. Biol., Vol. 16(11), pages 6486 to 6493. The phosphorylation sites can be prepared by means of commonly used methods of peptide synthesis.

According to a preferred embodiment the substance according to the invention, is designed in such a way, that when reacting with at least one cellular factor, the induction of the biological or/and detectable property is modified.

According to the invention, a cellular factor refers to any intracellular molecule such as for example a protein with a defined activity, that indirectly or directly interacts with the substance, and by doing so, modifies the induction of the biological or/and detectable property. A modification could mean, that the induction of the property as a result of the interaction with the cellular factor, is enhanced or even actually takes place. A modification can also mean that the induction of the property resulting from the reaction with the cellular factor, is reduced or does not take place at all.

This measure has the advantage that herewith the induction of the biological or/and detectable property is even better controlled. Furthermore, the substance can be designed in such a way, that it does only react with such a cellular factor that is present in a transformed or infected cell, and that the induction of the property is due to this reaction, enhanced. On the contrary, it is also possible to design a substance in such a way, that a reaction only takes place with such cellular factors which are present in a normal or healthy cell. By the latter measure, the substance according to the invention could be altered in such a way, that an induction of the biological or/and detectable property, which might occur due to unforeseen events even without the presence of the two molecules, is prevented. The therapeutical or diagnostic utility is further increased by this security measure.

According to the invention, it is further preferred if the cellular factor consists of an apoptotic or anti-apoptotic molecule or of the telomerase enzyme.

This measure provides an improvement of the selectivity and specificity of the substance according to the invention, for transformed or/and infected cells. It is known, that the telomerase is especially active in transformed cells, whereas no or merely weak telomerase activity can be detected in healthy cells. Comparable conditions apply to anti-apoptotic molecules. These are essentially active in transformed cells, but are not active or merely in much less degree in healthy cells. By an appropriate design of the substance according to the invention, the latter is increased in its ability to induce a biological or/and detectable property by the interaction with the telomerase or with anti-apoptotic molecules.

In transformed or in infected cells, pro-apoptotic mechanisms are very often inactivated. This occurs, inter alia, by the inactivation or the degradation of pro-apoptotic molecules which are mainly present or active in normal cells. By an appropriate design of the substance according to the invention, the latter will be altered after a reaction with pro-apoptotic molecules in that way, so that the induction of the biological or/and detectable property is no longer possible.

It is preferred if the substance according to the invention is designed in such a way, that its entrance or uptake into the cell or/and cellular compartments is enabled.

By this measure, it is assured that the substance in fact can induce the biological or/and detectable property in the interior of the cell or in the envisaged cellular compartments, such as for example the cytoplasma, or the nucleus. Such a design can be realized by providing a segment of the molecule, that mediates the permeability of the latter through the membrane, or by another segment that enables the passive or active transport of the substance into the cell.

This can also occur by providing an area or a segment in the molecule, which establishes the affinity and internalization of the substance for or into the cell, respectively, such as for example by means of an antibody that might be modified, or by an aptamer or another ligand, which are bound to the substance. By this measure, the selectivity of the substance is further increased. For example, ligands can be provided, which enable the entrance or uptake into very specific transformed or infected cells, such as cells of a particular tumor or cells which were infected by a particular pathogen. Therefor cell type-specific surface markers, for example tumor antigens, can be used to which ligands which are provided at the substrate according to the invention, bind in a selective manner. According to this preferred variation, the design of the substance can be realized by the packaging of the substance into a transport vesicle.

According to a preferred embodiment, the substance according to the invention is designed as a low-molecular weight active agent.

Low-molecular weight active agents are also referred to as "small molecules." This is a generic term for chemical substances having activities in biological systems. The molecular weights of these compounds are usually below about 1000 to 1200 Dalton, in some cases they can also be above that weight. The advantage of this measure is, that herewith the substance can be produced on a large scale by means of well established synthetic methods, and that the substance is sufficiently stable. Furthermore, chemically defined or biological matrices which are known in the art such as peptides can be used, and their properties can be optimized by chemical synthesis by using the so-called "rational drug design," which is also referred to as "molecular evolution" or "specificity evolution;" cf. Böhm et al. (2002), "Wirkstoffdesign," Spektrum Akademischer Verlag, Heidelberg. New developments in the field of the production of low molecular weight active agents have been summarized by Nature magazine (available on the website of Nature under the terms "horizon," "chemicalspace," and "highlights"), the content of which is incorporated into this application by reference.

It is preferred if the substance according to the invention is a peptide.

This measure is advantageous since in this case the substance can be produced in an easy manner by means of well known methods of peptide chemistry. The substance can be designed as a substrate for the two molecules in an easy way, for example by providing a segment comprising a phosphorylation site for the CDK2 kinase, and a segment comprising a phosphorylation site for the MAP kinase. Moreover, in this embodiment peptide segments can easily be provided, which confer upon the substance its permeability through the cellular membrane. These kinds of peptide segments are well known in the art, and consist preferably of a sequence of arginine residues.

Another advantage of the design of the substance according to the invention as a peptide consists in the fact, that a peptide is a suitable template or matrix for the preparation of a "small molecule". For example, a peptide can be synthesized having an affinity for the two molecules as well as the intended biological property, subsequently a co-crystal consisting of said peptide complexed with the two molecules can be obtained via standard methods. With the aid of said co-crystal, a corresponding low molecular substance can be derived by means of "molecular evolution" or "specificity evolution" in silico, which then, in turn, can be chemically synthesized on a large scale. This pathway which uses the peptide as a template for a corresponding "small molecule" and, therefore, as a kind of intermediate product of the substance according to the invention, is clearly predetermined for a skilled person.

An easy handling of the substance is also made possible by another embodiment according to the invention, by which segments are provided in the substance, which mediate a binding to an affinity column, as for example a segment comprising histidine residues, or a tag consisting of glutathion-S-transferase (GST). These segments or tags can be easily provided in a peptide. The separate functional segments can then, e.g., be connected to each other by connecting sequences, so-called "linkers". By the design of the substance as a peptide, therefore, a flexible and easy preparation according to the intended property is made possible.

The before-mentioned easy preparation of such peptides by which a user-defined reaction can be induced in the cell via a reaction with cell-owned molecules, is described in the art.

For example, Nguyen et al. (2004), "Caged Phosphopeptides Reveal a Temporal Role for 14-3-3 in G1 Arrest and S-phase checkpoint Function", Nature Biotechnology, Vol. 22, pages 993 to 1000, describe the preparation of a peptide construct that can be introduced into biological cells, and that shows a reaction with cell cycle-regulating molecules after an activation by UV radiation. The data presented there further proves the enablement of the present invention.

Another advantage of the substance being designed as a peptide consists in the fact, that a peptide can be easily prepared, mutated or otherwise altered by means of molecular biological methods, for example by using an expression vector in prokaryotic or eukaryotic expression systems. Therefore, a further subject of the invention also relates to an expression vector that encodes a corresponding peptide according to the invention. It goes without saying, that the expression vector according to the invention, can also comprise segments which enable or promote the expression in a cell type-specific manner, such as promoters, enhancers etc., or segments which enable a handling of the vector in the laboratory, such as for example segments which encode resistances against antibiotics, cleavage sites for restriction enzymes, polylinkers, etc.

It is also conceivable that the expression vector according to the invention, is directly used as a therapeutic or/and diagnostic substance. By means of an appropriate design, the expression vector is introducible into biological cells within which it is expressed. This design also has the advantage that nucleic acids are much more stable and robust compared to proteins and can be stored for an almost unlimited time. The expression vectors according to the invention are produced by methods described in the art. As an example for a corresponding manual the treatise of Joseph Sambrook and David W. Russel (2001), "Molecular Cloning—A Laboratory Handbook", Cold Spring Harbor Laboratory Press, Second Edition, can be cited, the content of which is herewith incorporated into the present application by referenced.

Preferably, the substance is designed in such a way, that the biological property has an either direct or indirect toxic effect on the transformed or/and infected cell.

By this measure, a substance is created which is selectively toxic for transformed or infected cells only, whereas it is largely safe for normal cells, since only the largely simultaneous reaction with the two molecules causes the induction of the toxicity, whereas a reaction with only one or none of the two molecules includes no or merely a negligible toxic activity.

A toxic property refers to such an activity which has a direct or indirect lethal effect on transformed or infected cells, for example by inducing apoptosis, necrosis, or oncosis, by inhibiting the metabolism, the signal transduction, the proteasom or the transcription activity, by interaction with the spindle apparatus of the cell, etc. A toxic property also refers to an activity which causes an arrest of the cell cycle or results in a well-aimed activation of the immune system or the expression of an antigenetic determinant, resulting in an attack on the transformed or infected cell.

The phosphorylation sites for the two molecules are preferably provided within the sequence of the p53 molecule or segments thereof.

By this measure it is meant that the sequence of the p53 molecule, preferably of the human variant, or one or several parts thereof, are a part of the substance according to the invention. This part comprises the phosphorylation sites for the two molecules, for example the two kinases which appear in transformed or infected cells in a largely simultaneous manner. Therefore, the phosphorylation sites can, for example, be embedded into the sequence of the p53 molecule, or can be provided by the phosphorylation sites which naturally are located within the p53 molecule, or can replace the natural phosphorylation sites of the p53 molecule.

The p53 molecule is a tumor suppressor protein that is regulated in its activity by phosphorylation events. The phosphorylation of the p53 protein causes an increase of its stability. In this case, the p53 protein acts as an active transcription factor and causes an activation of cell cycle-arresting proteins, such as $p21^{cip1}$, or the beginning of apoptosis.

With the provision of the phosphorylation sites for both kinases in the p53 molecules or functional segments thereof, for example of phosphorylation sites for the MAP and CDK2 kinase, a tool is created that displays p53-specific activities. For this, the substance is designed in such a way, that only in the case of a phosphorylation of both phosphorylation sites or of a phosphorylation of both phosphorylation sites at largely the same time, p53-specific activities are displayed, so that only in transformed or infected cells an arrest of the cell cycle or the beginning of apoptosis is induced.

According to a further embodiment, the substance is designed in such a way, that the detectable property is detectable by means of imaging methods.

This can, for example, be realized by designing the substance as a photoactivating molecule that emits a detectable signal after a reaction with the two molecules. The reaction of the substance according to the invention with the two molecules can also cause an activation of a further molecule which then emits a detectable property.

A suitable detectable property refers, for example, to luminescence or fluorescence, phosphorescence, bioluminescence, radioactivity or any other detectable signal. It is also, for example, possible to detect the reaction product that was generated by the reaction of the substance according to the invention with the two molecules, by the usage of antibodies or other ligands in a direct or indirect manner.

Within the frame of imaging procedures, methods such as tomography, FACS (fluorescence activated cell sorting), FRET (fluorescence resonance energy transfer), fluorescence microscopy, immunoblotting, ELISA, radiological methods, etc. can be used.

Another subject of the present invention relates to a composition, preferably to a pharmaceutical composition, that exclusively induces a biological or/and detectable property in a transformed or/and infected cell.

In the context of the invention, a property that is exclusively induced in transformed or/and infected cells refers to an induction that is at least largely if not totally avoided in normal cells, or an induction that can be tolerated in normal cells when considering the therapeutical or diagnostic benefits.

With their data the inventors give evidence for the first time, that a targeted and selective attack on transformed or infected biological cells is possible, whereas normal or healthy cells are almost completely unaffected. Furthermore, the inventors provide a substance or a composition, respectively, for the first time, that induces a biological or/and diagnostic property exclusively in transformed or/and infected cells in a highly selective manner. This has not been achieved in the art so far.

The composition preferably comprises the substance according to the invention, or the expression vector according to the invention, and, if appropriate, a pharmaceutical acceptable carrier. The production of such a pharmaceutical composition is well described in the art. In this connection the publication of Arthur A. Kibbe (2000), "Handbook of Pharmaceutical Excipients", American Pharmaceutical Association and Pharmaceutical Press, Third Edition, can be cited, the content of which is incorporated into the present application by reference. The choice of the appropriate concentration of the substance in the composition is up to the discretion of the skilled person and can be determined by means of simple experiments, for example by titration experiments. In most of the cases it is also necessary to determine the optimum concentration of the active agent individually, depending on the patient to be treated.

The composition according to the invention, preferably comprises activity enhancing agents. This includes all compounds which increase the induction of the biological or/and detectable property by the substance according to the invention. Appropriate activity enhancing agents for an application in vitro are tumor promoters, such as phorbole-12-myristate-13-acetate (PMA) or ionomycin. For an application in vivo cytostatics, antibodies such as herceptin or rituximab, or growth factors, such as G-CSF or FGF can be used. These activity enhancing agents are to be used in an appropriate concentration, so that the simultaneous appearance or activity of the at least two molecules is enhanced exclusively in the transformed or infected cells, whereas normal or healthy cells are not affected. Further appropriate activity enhancing agents used in the pharmaceutical substance according to the invention are, when a therapeutic application is intended, cytostatics which are well known in the art, or other active agents which are used in the therapy of cancer diseases or infections. Also so-called "sensibilizers", as for example bispecific antibodies, are possible activity enhancing agents.

Against this background, the substance according to the invention, or the expression vector according to the invention, can be used for the preparation of a pharmaceutical composition for the treatment of transformed or/and infected biological cells.

A further subject of the invention relates to a method for diagnosing a tumor disease or/and infection in a living being, comprising the following steps: (a) providing a biological sample to be analyzed; (b) analyzing the appearance of molecules in single cells of the biological sample, and (c) correlating the finding of essentially simultaneously appearing molecules in single cells of the sample, which exclusively appear essentially simultaneously in a transformed or/and infected biological cell, with a positive diagnosis.

According to the invention, a biological sample encompasses isolated cells and tissues as well as whole organisms, e.g. a human or animal being. The diagnostic method can be performed with isolated biological material in the laboratory, which means in vitro, but also with a living organism, i.e., in vivo or in situ.

A main advantage of this method is that, after a positive diagnosis has been made, information is obtained about which molecules in the transformed or infected cells do appear simultaneously compared to normal cells. This enables the physician in charge to apply therapeutic agents, even ordinary cytostatics, which specifically interact with the two molecules or interfere in the corresponding signal transduction pathways.

The analysis in step (b) is preferably performed by means of the so-called single cell profiling or FRET technology.

The method of single cell profiling that is for example described in Irish et al. (2004 l.c.), enables the analysis of intracellular events on a single cell level, such as the observation of molecules which appear simultaneously in the single cell, and activities of said molecules. Hereby for example the activity of enzymes or kinases can be measured in a single cell, By the single cell profiling method the formation of artifacts is avoided, which are induced during the analysis of cell cultures due to the methods used therein, for example by synchronizing the cells within the cell cycle. The cells to be analyzed can rather be analyzed against the background of their natural physiological cell cycle on a single cell level.

Within step (a) preferably a stimulation of the biological sample occurs by means of a tumor promoter, preferably by means of phorbole-12-myristate-13-acetate (PMA), ionomycin, a cytostatic, or an antibody, preferably herceptin or rituximab, or a growth factor, preferably G-CSF or FGF.

The inventors have realized that after a stimulation of the cells in vitro with such a tumor promoter, or in vivo with growth factors or cytostatics, a differentiation between transformed/infected biological cells and normal or healthy cells, is particularly easy. The substances herceptin and rituximab, for example, activate the ras/raf pathway via Her2/neu or CD20 respectively, and therewith additionally increase the kinase activity in the transformed and infected cells. For healthy CDC34 cells it has been found by the inventors, that after a corresponding stimulation the induction of kinase activities, for example of the MAP and CDK2 kinase activities, occurs in a distinctive chronological order, if compared to the induction of kinase activities in AML tumor cells, always on condition that single cells are analyzed. These differences which can be enhanced by such a stimulation, allow the diagnosis of a tumor disease or of an infection.

In the afore-described method preferably step (a) includes an incubation of a biological sample with the above-described substance according to the invention, or/and the above-described expression vector according to the invention. In this case step (b) includes the detection of the detectable property.

A further subject of the present invention relates to a method for the treatment of a tumor disease or/and infection in a living being, to which the above-explained substance according to the invention, or/and the above-explained expression vector according to the invention, is administered.

It goes without saying that the before-mentioned features and the features to be described below can be used not only in the combination indicated in each case, but also in different combinations or alone, without departing from the scope of the invention.

The subject matters of the present invention are now explained by means of examples which are of purely illustrative character and do not limit the teaching according to the invention. Thereby, reference is made to the attached FIG. 1:

DESCRIPTION OF PREFERRED EMBODIMENTS

Example 1

Figure 1:
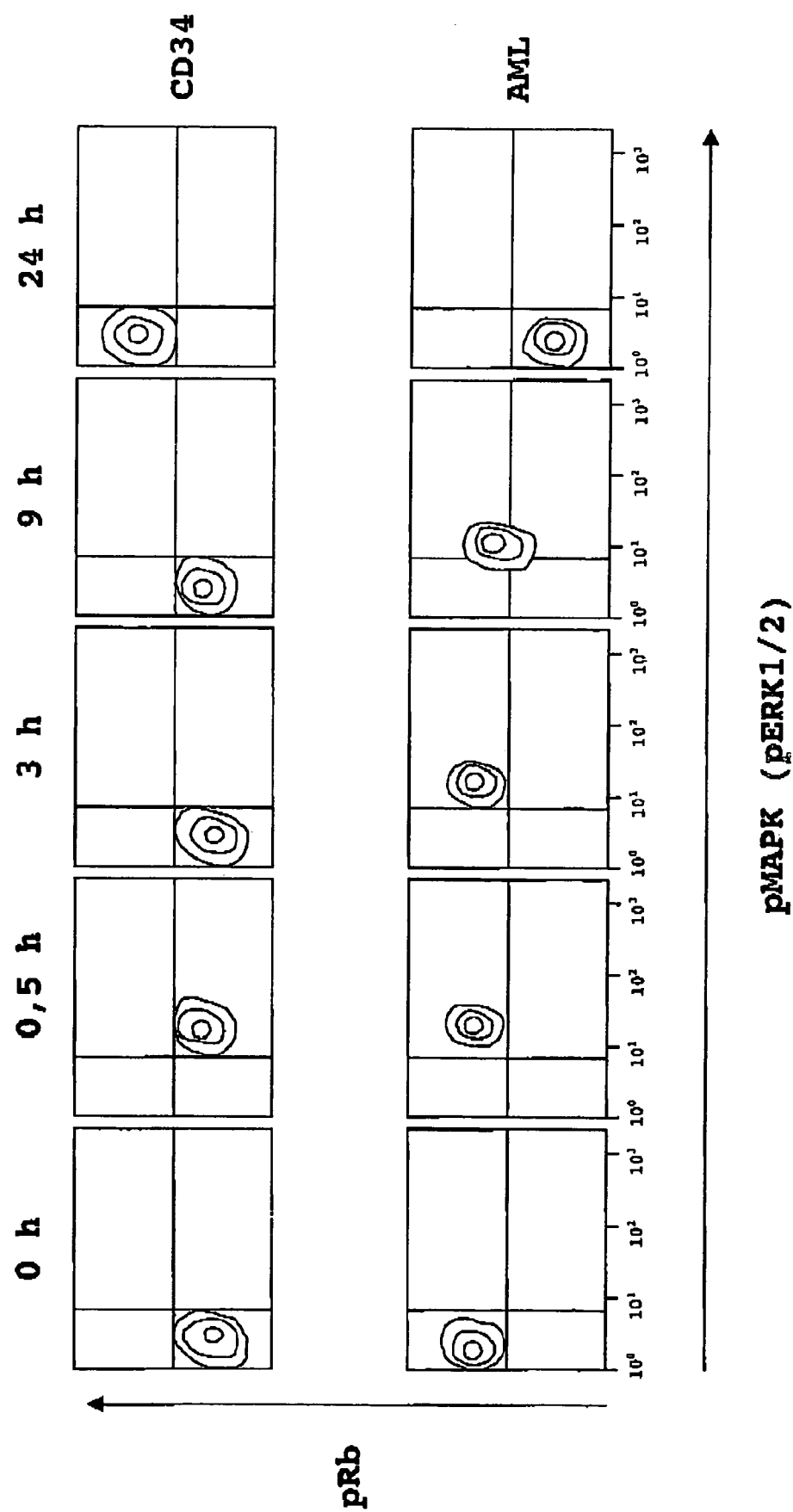
FIG. 1: Simultaneous progression of the ras/raf and the CDK2 signal pathways in transformed cells.

Differential Signal Transduction in Normal/Healthy Cells and in Transformed Cells CD34 positive blood stem cells were isolated by "magnetic cell sorting" (MACS). AML tumor cells were obtained from the peripheral blood of a patient suffering from acute myeloic leukemia (AML) M5 having >80% blasts, without any further manipulation.

All the cells were activated with PMA/ionomycin and, therewith, released into the cell cycle. Cells were fixed with formaldehyde at different time points after incubation, and their membranes were permeabilized with methanol.

Afterwards, the activities of the factors of the ras/raf signal pathway were analyzed via the phosphorylation state of the MAP kinase (pMAPK or pERK1/2), and the activities of the factors of the CDK2 signal pathway were analyzed via the phosphorylation state of the retinoblastoma protein (pRB), a substrate of the CDK2 kinase.

For this the method of fluorescence activated cell sorting (FACS) was used, by means of which single cells can be analyzed. This method is described in detail in Irish et al. (2004, l.c.). For this method, the permeabilized cells were incubated with an anti-phospho-Rb/PE-anti-mouse antibody, which specifically binds to phosphorylated Rb proteins followed by an incubation with a FITC-conjugated anti-MAP-kinase antibody, which specifically binds to phosphorylated MAP kinase (ERK 1/2).

The results of this experiment are illustrated in the graph of FIG. 1. In this figure representative two-dimensional blots resulting from the FACS analysis are schematically represented. On the x-axis the increasing phosphorylation of the MAP kinase is shown, whereas on the y-axis the increasing phosphorylation of Rb is shown. In order to simplify the orientation of the alterations of the signals, the blots have drawn-in intersecting lines.

It can be seen from the blots, that in normal CD34 cells after 30 min, which could correspond to the early G1 phase, the MAP kinase is present in its phosphorylated state. This is shown by a shift of the measured signal to the right. On the other hand, Rb is not in its phosphorylated state at that time, a shift of the measured signal into the upward direction did not take place.

In normal CD34 cells a phosphorylation of Rb did not take place until approximately 24 hours, which might correspond to the late G1 or early S phase where the MAP kinase is again in its non-phosphorylated state (FIG. 1, upper row). At even later measurements which are not shown in FIG. 1, Rb is again in its non-phosphorylated state.

This observation in normal/healthy cells is in compliance with the knowledge in the art: in the early G1 phase the ras/raf pathway is activated as demonstrated by the phosphorylation and activation of the MAP kinase. In the late G1 or early S phase, respectively, the MAP kinase is again inactive and therefore in its non-phosphorylated state. However, at this point in time the CDK2 signal pathway is activated, resulting in an active form of the CDK2 kinase, which is first found complexed with cyclin E and then complexed with cyclin A, and which phosphorylates different substrates, such as for example the pRB protein. However, the MAP kinase and the CDK2 kinase are never simultaneously active.

The phenomena observed in the transformed cells were completely unexpected and are herein shown for the very first time. The kinetics of the activation of the ras/raf and CDK2 signal transduction cascades are strongly altered compared to the kinetics of the corresponding activation in normal cells. The Rb protein is found in its already phosphorylated state at the first measuring point (t=0 h). So it can be concluded, that the CDK2 kinase is already in its active form. This is shown by an upward shift of the measured signal. Furthermore, the phosphorylated form of the Rb protein could be detected by radioimmunological methods or other means known in the art. Even 30 min after the stimulation, the MAP kinase also appears in its phosphorylated state besides Rb. This is shown by a shift of the measured signal to the right. This simultaneous phosphorylation of the Rb protein and the MAP kinase can be detected over long times during the measuring period. It is not until the 24 h measuring time point, that both the Rb protein as well as the MAP kinase both are back again in their non-phosphorylated states (FIG. 1, lower row).

This difference between normal and transformed cells can also be observed without previous stimulation of the cells, in which case the simultaneous phosphorylation of the Rb protein and the MAP kinase in transformed cells is less noticeable.

Therefore, in the transformed cells one can surprisingly find an essentially simultaneous progression of both the ras/raf pathway as well as of the CDK2 pathway, even immediately after the release of the cells into the cell cycle. Active MAP kinase as well as active CDK2 kinase can be detected essentially simultaneously in the transformed AML cells. The chronologically different appearances of the active MAP kinase (early measurement, 0.5 h) and the active CDK2 kinase (late measurement, 24 h) in the cell cycle, that can be observed in normal cells, is therefore no longer present. Both activities are present at the same time.

Example 2

Preparation of the Substance According to the Invention (a) As a Low-Molecular Weight Active Agent ("Small Molecule")

Basically, the preparation of low-molecular weight active agents is well described in the art and ranks among the tools of a clinical chemist; cf. Böhm et al. (2002, l.c.). Especially, a large number of methods is described, by which such low-molecular active agents can be prepared, which react with signal transduction molecules such as kinase inhibitors; Buchdunger et al. (1995), "Selective Inhibition of the Platelet-Derived Growth Factor Signal Transduction Pathway by a Protein-Tyrosine Kinase Inhibitor of the 2-Phenylamino-pyrimidine Class", Proc. Natl. Acad. Sci. USA, Vol. 92, pages 2558 to 2562; Druker et al. (1996), "Effects of a Selective Inhibitor of the Abl Tyrosine Kinase on the Growth of Bcr-Abl positive Cells", Nat. Med., Vol. 2, pages 561 to 566; Schindler et al. (2000), "Structural Mechanism for STI-571 Inhibition of Abelson Tyrosine Kinase", Science, Vol. 289, pages 1938 to 1942. A further publication describes exemplarily for imatinib the preparation of a "small molecule": Thomas Fischer (2002), "Der Signalhemmer Imatinib Mesilat (STIS571)—Wirkprinzip und klinische Anwendung", published by UNI-MED, Bremen, Germany. The contents of these publications are herewith incorporated into the present application by reference.

By using the methods described in before-mentioned publications the skilled person is able to prepare the substance according to the invention, without any undue burden. Starting from preconstructed peptides as templates, small molecules can be designed by means of "molecular evolution" or "specificity evolution", said peptides comprise segments by which a selective contacting with specific cellular kinases can occur. These segments or parts of the molecule, which derive from the peptide template, interact, for example, with the ATP binding site or the active center of the kinases. The molecule can be designed in such a way, that an activation which causes an induction of a toxicity or of a detectable signal, only occurs if an essentially simultaneous interaction with the ATP binding sites or the active centers of both kinases, i.e. the HAP kinase and the CDK2 kinase, takes place. Therefor crystal structures of the MAP kinase and the CDK2 kinase might be needed which are accessible in public databases.

(b) As a Peptide

The substance according to the invention can be prepared by means of commonly used peptide synthesis methods, resulting in the following structure: histidine residue-membrane permeable sequence-linker-CDK2 substrate-linker-MAP kinase substrate. The N terminus is situated on the left side, the C terminus is situated at the right side. A conceivable amino acid sequence reads: HHHHHH-RRRRRRRRR-GG-HHASPRK-GG-TGPLSPGPF. In this representation the standardized one-letter code for amino acids is used. This sequence can also be modified, so that the substance is activated in the case of a double-phosphorylation of both substrates, resulting in the induction of a toxicity or a detectable signal. In order to assure this result, further segments or molecules or molecule sections can be provided, which are activated by a simultaneous phosphorylation of both substrate segments of the substance.

The functioning of the substance can be verified in a mouse model. This is described in the publication of Traggiai et al. (2004) "Development of a Human Adaptive Immune System in Cord Blood Cell-transplanted Mice", Science, Vol. 304 (5667), pages 104 to 107. By means of this model, the double-phosphorylation of the substance in transformed cells can be proven. This publication is incorporated into this application by reference.

In this model, mice with normal human immune system are generated. This model can be modified so that mice with human AML are generated, within which the double-phosphorylation of the substance according to the invention, can be shown.

Of course, other designs of the substance according to the invention, are conceivable, for example substrate segments can be designed in that way, so that a toxic activity is induced after an enzymatic conversation of the substrate segments.

Example 3

Diagnosis of a Tumor Disease by Means of the Substance According to the Invention Blood is taken from a patient suffering from leukemia and can be, if appropriate, treated or cultivated according to methods well known in the art.

Subsequently, the blood cells are incubated with the substance obtained as described in example 2. The substance is designed in such a way, that it is double-phosphorylated in case of the simultaneous presence of the MAP kinase and the CDK2 kinase. In case of the presence of only one of the two kinases or of a distinct different chronological appearance of the two kinases, the substance is merely single-phosphorylated.

For this purpose, the substance is designed as a "biosensor" for its usage in the FRET (fluorescence resonance energy transfer) technology. Suitable FRET pairs, for example coumarin and fluorescein, are provided, so that in case of a double-phosphorylation of the substance the conformation of the substance is changed, resulting in both FRET pairs being located in direct vicinity, further resulting in the emittance of a detectable signal. The construction of such a substance lies within the ability of a specialist, methods suitable therefore within the ability of a specialist, methods suitable therefore are already commercially available in form of construction kits. An example thereof is the Z'-LYTE™ assay of the company Invitrogen (available on the website of Invitrogen). The content of the description of this assay is incorporated into the present application by reference.

After the incubation the cells are lysed. The lysate is treated with protease. Afterwards, the FRET signal is read. In this connection also a usage in the FACS and a single cell profiling (cf. Irish et al. (2004), l.c.) can be carried out.

In the case of the detection of a signal that indicates a double-phosphorylation, the diagnosis is positive.

Another appropriate method for preparing the diagnostic substance according to the invention, is described in Chi-Wang Lin and Alice Y. Ting (2004), "A Genetically Encoded Fluorescent Reporter of Histone Phosphorylation in Living Cells", Angew. Chem. Int. Ed., Vol. 43, pages 2940 to 2943. The content of the publication is incorporated into the present application by reference.

Therefore, what is claimed, is:

1. Method for diagnosing a tumor disease and/or an infection in a living being in vitro, comprising:
   (a) providing leucocytes to be analyzed from said living being,
   (b) analyzing in said leucocytes the phosphorylation state of a retinoblastoma protein involved in the regulation of the cell cycle and the phosphorylation state of a MAP kinase involved in the regulation of the cell cycle, wherein said retinoblastoma protein is involved in the regulation of the cell cycle at a first time in normal cells and said MAP kinase is involved in the regulation of the cell cycle at a second time in normal cells, and
   (c) correlating the finding of simultaneous phosphorylation states of said retinoblastoma protein and said MAP kinase in said leucocytes with a positive diagnosis.

2. Method for diagnosing a tumor disease and/or an infection in a living being in vitro, comprising:
   (a) providing single cells to be analyzed from said living being,
   (b) analyzing in said single cells the activity of a substrate of the CDK2 signal pathway involved in the regulation of the cell cycle and the activity of a substrate of the ras/raf signal pathway involved in the regulation of the cell cycle, wherein said substrate of the CDK2 signal pathway is involved in the regulation of the cell cycle at a first time in normal cells and said substrate of the ras/raf signal pathway is involved in the regulation of the cell cycle at a second time in normal cells, and
   (c) correlating the finding of simultaneous activities of said substrate of the CDK2 signal pathway and said substrate of the ras/raf signal pathway in said single cells with a positive diagnosis.

3. Method according to claim 2, wherein:
   (i) the substrate of the CDK2 signal pathway is a retinoblastoma protein; and,
   (ii) the substrate of the ras/raf signal pathway is a MAP kinase.

4. Method according to claim 3, wherein:
   (i) the activity of the retinoblastoma protein is the phosphorylation state of the retinoblastoma protein; and,
   (ii) the activity of the MAP kinase is the phosphorylation state of the MAP kinase.

5. Method according to claim 2, wherein the single cells are leucocytes.

* * * * *